United States Patent [19]

Chang et al.

[11] 4,138,440

[45] Feb. 6, 1979

[54] CONVERSION OF LIQUID ALCOHOLS AND ETHERS WITH A FLUID MASS OF ZSM-5 TYPE CATALYST

[75] Inventors: Clarence D. Chang, Princeton; Solomon M. Jacob, Cherry Hill, both of N.J.; Anthony J. Silvestri, Morrisville, Pa.; John C. Zahner, Princeton, N.J.

[73] Assignee: Mobil Oil Corporation, New York, N.Y.

[21] Appl. No.: 497,429

[22] Filed: Aug. 14, 1974

[51] Int. Cl.$^2$ .............................................. C07C 1/24
[52] U.S. Cl. .............................. 260/668 R; 208/118; 260/120; 260/125; 260/141; 260/668 A; 260/671 R; 260/672 T; 260/673; 260/676 R; 260/677 R; 260/682
[58] Field of Search .................. 260/668 R, 682, 676, 260/671, 677, 672 T, 668 A; 208/135, 141, 118, 120

[56] References Cited

U.S. PATENT DOCUMENTS

| | | | |
|---|---|---|---|
| 2,418,003 | 3/1947 | Angell | 208/118 |
| 3,728,408 | 4/1973 | Tobias | 260/668 C |
| 3,856,873 | 12/1974 | Burress | 260/672 T |
| 3,894,107 | 7/1975 | Butter et al. | 260/673 |
| 4,046,825 | 9/1977 | Owen et al. | 260/668 R |
| 4,071,573 | 1/1978 | Owen et al. | 260/668 R |

Primary Examiner—Veronica O'Keefe
Attorney, Agent, or Firm—Charles A. Huggett; Carl D. Farnsworth

[57] ABSTRACT

The conversion of alcohols and ethers to gasoline boiling constituents with HZSM-5 catalyst in a fluid catalyst system is arranged for reactant plug flow wherein the reaction temperature is controlled by the heat of vaporization of liquid reactant charged to the reactor. Vaporization of the reactant with recycled catalyst in acceptable ratios restricts reaction temperatures to within acceptable limits.

5 Claims, 1 Drawing Figure

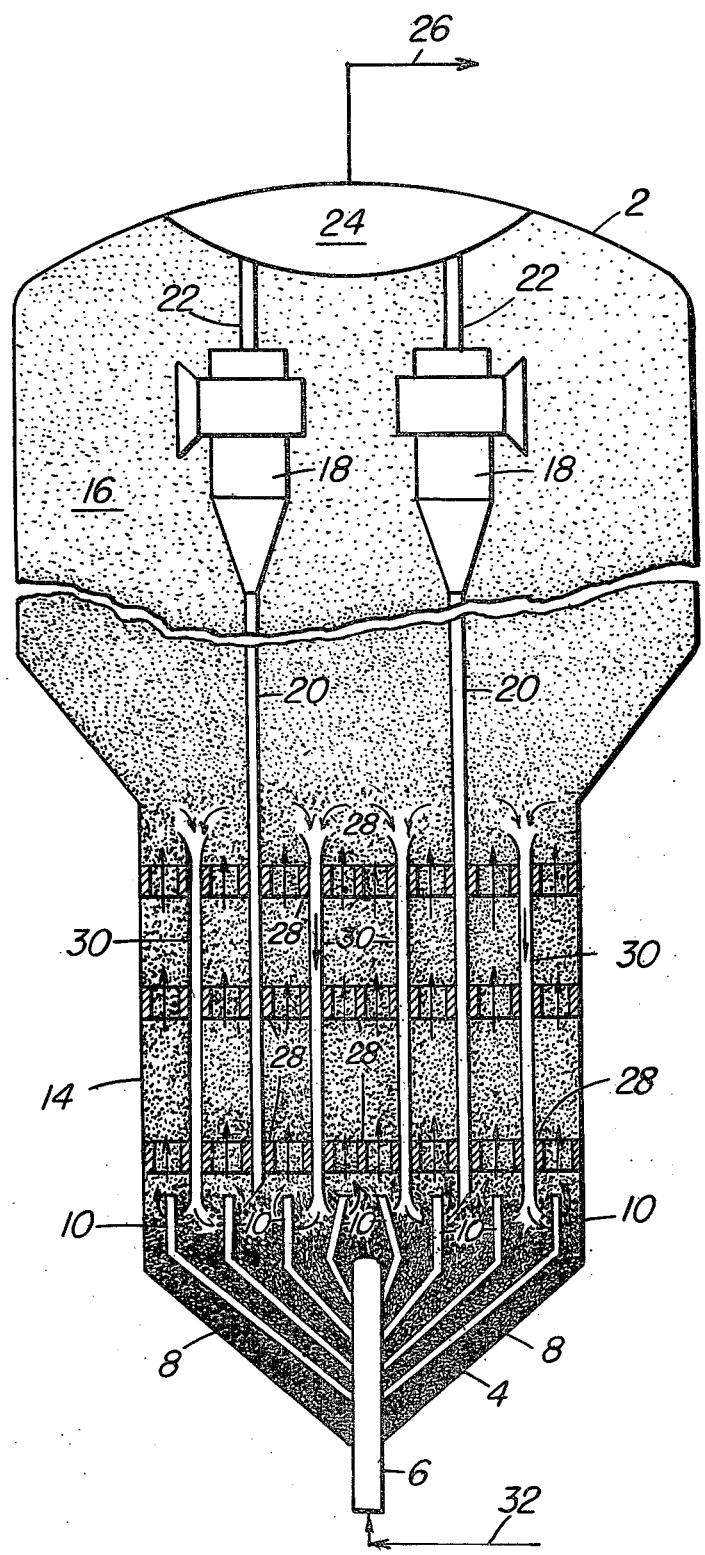

CONVERSION OF LIQUID ALCOHOLS AND ETHERS WITH A FLUID MASS OF ZSM-5 TYPE CATALYST

BACKGROUND OF THE INVENTION

The application of fluidized-catalyst techniques developed particularly in the petroleum industry for effecting chemical reaction embodying the distribution of heat and/or the disposal of undesired heat has long been accepted as a major processing tool of the industry. For example, the catalytic cracking of oil vapors to produce lower boiling desired products and regeneration of the catalyst used in such an operation has been particularly useful in fluidized catalyst techniques. It has also been proposed to use the fluidized catalyst technique in the highly exothermic reactions of Fischer-Tropsch synthesis and the known Oxo process primarily for the disposal of generated heat. In many of the fluidized catalyst operations developed, disposal of the reaction heat has been accomplished by many different techniques including transfer of catalyst through cooling sections and/or including indirect cooling means with a fluid bed of catalyst to adsorb reaction heat transferred by the finely divided fluidized catalyst particles. Not only is the fluidized catalyst technique used for temperature control by addition and/or removal but it has also been found useful for extending the active life of the catalyst used in the process.

The present invention is concerned with an arrangement and method of operation for disposing of generated exothermic reaction heat within limits which will particularly protect and prolong the useful life of the catalyst employed in the operation.

SUMMARY OF THE INVENTION

This invention relates to the method and means for effecting chemical reactions in the presence of crystalline zeolites. More particularly, the present invention is concerned with effecting exothermic chemical reactions in the presence of high silica to alumina ratio crystalline zeolites particularly promoting the formulation of hydrocarbon product materials higher boiling than the reactant charge material.

This invention relates to the catalytic restructuring of alcohols and ethers. The present invention is directed to the catalytic restructuring of methanol and dimethyl ether to form a desired aromatic rich product in a reactant plug flow type of operation. In a more particular aspect the present invention is directed to a temperature restrained catalytic restructuring of alcohols and ethers to form aromatics wherein temperature restriction is accomplished by either direct or indirect heat exchange arrangement or a combination of both. In yet another aspect the present invention is directed to a selection and arrangement of operating conditions designed particularly for the chemical rearrangement of either methanol or dimethyl ether alone or in combination with one another to form gasoline boiling range aromatics in preference to the formation of durene.

In a further aspect the present invention is concerned with effecting the conversion of alcohols and ethers with a fluid mass of particulate material comprising a crystalline zeolite providing a pore dimension greater than about 5 Angstroms and pore windows of a size provided by 10 membered rings of oxygen atoms.

In the present invention a chemical reactant selected from the group consisting of methanol, ethanol and their corresponding ethers or a mixture of alcohol and ether is admixed with a quantity of a particular crystalline zeolite catalyst composition of desired activity and selectivity characteristics to provide a mix temperature of at least 500° F. The thus formed mixture is passed in reactant plug flow condition through a temperature restrained reaction path not to exceed an outlet temperature of 1000° F. Temperature restraint of the formed mixture is accomplished, through vaporization of liquid feed for example, an alcohol feed. The use of a restricted reaction path promoting reactant once through contact with catalyst in temperature restricted heat exchange is essential to the combination of the invention. Recirculation of hot catalyst to accomplish vaporization of the liquid feed is most important. Thus back mixing of catalyst may be permitted in the operation but not reactant or product of the reaction in order to minimize durene formation. A further desired restraint on the reactant plug flow operation of this invention is concerned with the selection of operating conditions which will particularly avoid the presence of any large excess of the reactant material in the product effluent of the reaction zone.

The present invention is concerned with a selection of operating conditions which will provide a chemical rearrangement of alcohols and ether reactants to form gasoline boiling range materials rich in isoparaffins and aromatics, as well as by product gases rich in olefins and isobutane. The olefins and isobutane are particularly desirable for sulfuric acid and HF alkylation processes for producing a gasoline blending product material.

An important characteristic of the crystal structure of this novel class of zeolites is that it provides constrained access to, and egress from, the intracrystalline free space by virtue of having a pore dimension greater than about 5 Angstroms and pore windows of a size provided by 10-membered rings of oxygen atoms. It is to be understood, of course, that these rings are those formed by the regular disposition of the oxygen of the tetrahedra making up the anionic framework of the crystalline aluminosilicate, the oxygen atoms themselves being bonded to the silicon or aluminum atoms at the centers of the tetrahedra. Briefly, the preferred novel type or class of crystalline zeolite catalyst useful in this invention possess, in combination: a silica to alumina ratio of at least about 12; and a structure providing constrained access to the crystalline free space.

The silica to alumina ratio referred to may be determined by known analysis techniques. The silica-alumina ratio is meant to represent, as closely as possible, the ratio in the rigid anionic framework of the zeolite crystal and to exclude aluminum in the binder or in cationic form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. exhibit "hydrophobic" properties.

The type of zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight membered rings of oxygen atoms, then access to molecules of larger cross-section than normal hexane is excluded and the zeolite is not of the desired type. Windows of ten-membered rings are preferred, although excessive puckering or pore blockage may render these catalysts ineffective. Twelve-membered oxygen rings do not generally appear to offer sufficient constraint to produce the advantageous conversions, although structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e. 1 volume of hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons. Catalysts suitable for the present invention are those having a constraint index from 1.0 to 12.0, preferably 2.0 to 7.0.

The class of crystalline zeolites defined herein is exemplified by ZSM-5, ZSM-11, ZSM-12, ZSM-21, TEA mordenite and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in West German Offenlagunschrift No. 2,213,109, the entire contents of which are incorporated herein by reference.

The specific crystalline zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type of zeolite catalyst by various activation procedures and other treatments such as base exchange, steaming, alumina extraction, calcination and combinations thereof. Naturally occurring minerals which may be so treated include ferrierite, brewsterite, stillbite, dachiardite, epistilbite, heulandite and clinoptilolite. The preferred crystalline aluminosilicates are ZSM-5, ZSM-11, ZSM-12, ZSM-21 and TEA mordenite, with ZSM-5 particularly preferred.

The catalysts useful in this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst. For example, a completely sodium exchanged H-ZSM-5 is not catalytically operative.

In a preferred aspect, the catalysts are selected from those having a crystal density, in the dry hydrogen form, of not substantially below about 1.6 grams per cubic centimeter. It has been found that zeolites which satisfy the criteria herein identified are most desired because they tend to maximize the production of gasoline boiling range hydrocarbon products. Therefore, a preferred catalyst is one having a constraint index as defined above and selected from within the range of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on page 11 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

A remarkable and unique attribute of the class of zeolites above identified is the ability to convert paraffinic hydrocarbons to aromatic hydrocarbons in exceptionally attractive yields by contact at temperatures selected from within the range of 800° F. to about 1500° F. relying upon space velocities within the range of 1 to 15 weight hourly space velocity (WHSV). This class of crystalline zeolite appears to exert little, if any, action upon destroying aromatic rings either present in the feed or formed in the operation. They do, however, have the ability, with or without added hydrogen to cause paraffin fragments to dimerize and/or cyclize and also to alkylate aromatic rings either charged or formed in the operation. It appears that the operative ranges for alkylation and formation of new aromatic rings overlap but that the optimum ranges are relatively distinct; aromatization occurring at a higher temperature.

In copending Patent Application Ser. No. 387,223, filed Aug. 9, 1973, now U.S. Pat. No. 3,894,107 there is described a process for converting various aliphatic hetero compounds comprising alcohols, halides, mercaptans, sulfides and/or amines to their corresponding analagous compounds and aromatics with a ZSM-5 type of crystalline zeolite. The aromatization of alcohols is particularly discussed.

In copending Patent Application, Ser. No. 387,222, filed Aug. 9, 1973, now U.S. Pat. No. 3,894,106 there is described a process for converting particularly aliphatic ethers to higher molecular weight materials such as gasoline by contact with a ZSM-5 type of crystalline zeolite.

In copending Patent Application Ser. No. 387,224, filed Aug. 9, 1973, now U.S. Pat. No. 3,907,915 there is described a process for converting carbonyl type compounds such as acetone to aromatics and higher boiling materials by contact with a ZSM-5 type of crystalline zeolite.

The subject matter and contents of the above identified copending applications are intended to be incorporated herein by reference thereto.

The present invention is concerned with a method and system for effecting the conversion of alcohols such as, methanol and ethanol as well as their ethers to aromatics and isoparaffins. More particularly, the present invention relates to the method of effecting the exothermic conversion of liquid alcohols and ethers to gasoline boiling range products by selectively contacting a crystalline zeolite catalyst under conditions promoting the reaction desired and the efficient dispersal of generated exothermic reaction heat.

The conversion of alcohols (methanol) to gasoline boiling products using a HZSM-5 type crystalline zeolite is an exothermic reaction releasing approximately 750 Btu/pound of reactor charge. This heat release results in an adiabatic temperature rise up to approximately 1050 or 1100° F. The reaction may be carried out in a sequence of fixed catalyst bed reaction zones with intermediate quench between zones but such an operation is less flexible than a fluid catalyst operation and provides a temperature control problem.

A desirable alternative to a fixed catalyst bed arrangement is in the use of a relatively dense upflowing fluid catalyst system arranged for reactant plug flow operation controlled within specific limits and operating parameters. That is, the flow of catalyst and particularly the reactant feed and products of reaction are caused to move through the reaction zone without backmixing. It has been found when using liquid alcohol such as methanol as a feed, that the heat of vaporization of methanol, 471 Btu/pound, is sufficient to contain the adiabatic conversion temperature rise thereof to about 560° F. Therefore providing liquid methanol at a temperature within the range of 100°-150° F. as charge to an upflowing relatively dense fluid catalyst system arranged for catalyst recycle in the fluid bed system will operate to maintain through vaporization of the liquid feed upper operating temperature limit within the range of about 660° F. to about 710° F. In such a liquid feed system or one which is only partial vapor, the recycled catalyst is relied upon to vaporize the liquid feed and its heat of vaporization is sufficient to self limit the exothermic reaction. In such an operation the reaction is self-quenching since it relies upon the recycled catalyst essentially for bringing the liquid feed to reaction temperature.

The conversion of methanol to gasoline in the presence of a ZSM-5 type of crystalline zeolite proceeds most favorably at the herein identified operating temperature conditions. The operating temperatures may be within the range of 550° F. to about 900° F. and preferably are confined within the range of 650° F. to about 750° F.

In the operation particularly contemplated by the present invention it is desired to minimize the formation of durene or 1,2,4,5 tetramethylbenzene since it is considered an undesirable gasoline component because of its high melting point (approximately 175° F.). The formation of durene has been found to increase with pressure, reactant backmixing and in reactant by passing operations. Thus it is desirable to operate the fluid system of this invention at a relatively low pressure preferably less than 60 psig but at a pressure of at least about 15 psig. Pressures less than 50 psig are preferred.

The fluid system of the present invention relies upon a controlled upflowing fluid catalyst bed operation particularly promoting reactant plug flow operation, it being desirable to restrict the reactant space velocity to within the range of 1 to 3 feet per second and preferably not over 2 feet per second and under conditions which severely restrict the reactant forming gas bubbles promoting reactant bypassing. In essence the method and system of the present invention is maintained under three essential operating restraints comprising (1) substantially liquid feed with only partial vapor feed, (2) a catalyst temperature, reactant temperature and mix ratio sufficient to vaporize the liquid feed and (3) the reactant plug flow with minimum bypassing discussed above. These operating constraints are essential to the dense fluid bed operation of the present invention. In addition it has been found that the liquid alcohol feed can contain as much as 20% or more water and crude methanol obtained from natural gas and coal can be charged directly to the fluid bed operation without passing through a distillation column for water removal.

The catalyst employed for vaporizing the feed may be hot catalyst separated from the exothermic reaction product and recycled for this purpose through external or internal catalyst recycle means suitable for the purpose. The catalyst recycle and ratio to reactant feed must be sufficient to provide an initial reaction temperature at about 500° F. and preferably 650° F. Although the catalyst reactant mixture passed through a reaction path may encounter a significant catalyst slip factor it should not interfere with maintaining reactant plug flow operation in the absence of significant reactant-catalyst bypassing. The operating constraints above identified operate to reduce unreacted alcohol in the product effluent and the formation of large amounts of durene. The formation of durene is preferably restricted to less than 10 wt. percent of hydrocarbon product.

BRIEF DESCRIPTION OF THE DRAWING

The drawing shows diagrammatically in elevation one arrangement of an upflowing fluid catalyst system with catalyst recycle provided with a plurality of vertically restricted and adjacent reaction paths promoting plug flow conversion of vaporized reactant under restricted condition of reactant bypassing catalyst contacts. The arrangement of the drawing assures essentially an upflowing relatively dense fluid catalyst mass of desired catalyst backmixing but reactant once through plug flow to minimize reactant vapor bubble formation promoting reactant bypassing conditions.

DISCUSSION OF SPECIFIC EMBODIMENTS

Referring now to the drawing, there is shown diagrammatically in elevation an elongated reactor vessel 2 of larger diameter in an upper portion than in the lower portion thereof. The smaller diameter portion of the vessel 2 is provided with a conical bottom 4 into which extends a distributor pipe or manifold 6. The distributor manifold 6 is provided with a plurality of outwardly and upwardly extending liquid distributor pipes 8 provided with a nozzle 10 on the discharge end of each pipe. Relatively inert packing material is provided in the conical bottom portion of the vessel, in between the liquid distributing pipes. Above the liquid distributor arrangement above briefly identified there is maintained a fluid mass of catalyst particles 14 comprising a ZSM-5 crystalline zeolite dispersed in a suitable matrix material as herein provided. The fluid bed of catalyst occupies a major portion of the smaller cylindrical section of the reactor vessel and is caused to flow generally upwardly therethrough as a plurality of parallel streams of catalyst by introduced reactant into a superimposed dispersed phase of catalyst 16 in the upper enlarged portion of the reactor vessel.

A plurality of first and second sequentially arranged cyclonic separating means represented by means 18 is provided in the upper dispersed catalyst phase to effect a rapid cyclonic separation of entrained catalyst particles from product and unconverted reactant vapors. Catalyst particles separated by a change in upflowing reactant velocity and cyclonic means 18 are returned to a lower or bottom portion of the dense fluid bed of catalyst by dipleg 20 and downcomer 30. Separated vaporous material pass by conduit 22 from cyclonic means 18 to a plenum chamber 24 and thence by conduit 26 to product recovery equipment not shown.

As shown by the schematic drawing the reactor is provided with some apparatus internals arranged particularly to assure a desired upflowing fluid phase of catalyst through a plurality of reactant dispersal means such as grids; screens or any other device promoting the reaction and operating system restraints herein identified. Thus the reactor is provided within the smaller diameter portion thereof with a plurality of vertically spaced apart horizontally disposed gas bubble-catalyst dispersal means which promotes reactant plug flow (no reactant recycle) with a relatively dense upflowing fluid mass of catalyst under selected temperature conditions. The gas bubble dispersal means 28 may be essentially any solid gas or vapor distributor means spaced apart from one another throughout the catalyst bed height which will be effective for breaking up any formed relatively large gas bubbles so that a more intimate contact (no bypassing) may be maintained between reactant vaporous material and finely divided catalyst particles. Thus deep channel grid means, horizontally disposed pipe means positioned to provide a tortuous path for upflowing catalyst and gasiform material may be employed or bed spring type distributor means may be employed within the dense fluid catalyst section of the vessel. A plurality of catalyst downcomers or standpipes 30 are provided in the cross-section of the dense fluid catalyst portion of the vessel to circulate desired amounts of hot catalyst from an upper portion of the bed directly to a lower portion of the bed of catalyst to vaporize the liquid reactant introduced by inlet nozzles 10.

In the system and apparatus above defined, it is proposed to place the catalyst downcomer pipes and cyclone dipleg pipes in adjacent vertical sections and arranged to accommodate a plurality of downcomer pipes 30 in separate vertical sections to assure distribution of sufficient hot catalyst to vaporize liquid feed introduced throughout the lower cross-section of the fluid mass of catalyst.

In the arrangement of the figure, liquid methanol introduced by conduit 32 to manifold 6 is distributed by conduits 8 and nozzles 10 into a relatively dense fluid bed of ZSM-5 catalyst 14 for flow upwardly with catalyst particles under methanol vaporization and temperature conversion conditions at a velocity providing reactant plug flow operation through bubble breaking grid means encouraging some catalyst backmixing in the upflowing suspension between grid means.

EXAMPLE 1

Methanol was passed through a fluid catalyst microreactor at 1LHSV, 700° F. and 760 Torr. Fluidization was achieved by mechanical vibration of the microreactor by means of a vibrator. By proper adjustment of the vibrational amplitude, the catalyst particles could be kept in a state of turbulent suspension, filling the entire volume of the reactor. Liquid product was collected in wet and dry ice traps and gas was collected over saturated brine. Analyses were made by gas chromatograph and spectroscopic analysis. Results obtained as presented in Table 1 along with results obtained from a fixed bed reactor under identical conditions for comparison. It can be seen from the data of Table 1 that the fluid bed backmixing operation exerts a pronounced effect on durene production when compared with the plug flow operation.

TABLE 1

| Methanol Conversion over HZSM-5 | | |
|---|---|---|
| | Plug Flow | Backmix |
| Reactor Configuration | Fixed Bed | Fluid Bed |
| Temperature, ° F. | 700 | 700 |
| Pressure, PSIG | 0 | 0 |
| LHSV | 1 | 1 |
| Product Yield, wt. % | | |
| Hydrocarbons | 42.49 | 48.09 |
| $H_2O$ | 55.22 | 43.23 |
| $H_2$ | 0.05 | 0.06 |
| CO | 0.11 | — |
| $CO_2$ | — | — |
| Methanol | 0.12 | 4.34 |
| Dimethyl ether | 2.98 | 0.04 |
| Hydrocarbon Distribution, wt. % | | |
| Methane | 0.70 | 0.45 |
| Ethane | 0.50 | 0.80 |
| Ethene | 0.42 | 2.42 |
| Propane | 16.50 | 21.75 |
| Propene | 0.95 | 3.78 |
| i-Butane | 16.19 | 12.59 |
| n-Butane | 5.00 | 2.76 |
| Butenes | 0.44 | 3.16 |
| i-Pentanes | 7.05 | 7.22 |
| n-Pentane | 1.22 | 1.12 |
| Pentenes | 0.18 | 0.70 |
| $C_6$ P + O | 6.27 | 4.02 |
| $C_7$ P + O | 0.87 | 0.63 |
| $C_8$ + P + O | 0.35 | 1.68 |
| Total Aromatics | 43.35 | 36.94 |
| Durene | 1.90 | 6.42 |

EXAMPLE 2

Methanol was passed in contact with ZSM-5 catalyst at a WHSV (Weight Hourly Space Velocity — total catalyst basis) of 0.53 at a temperature maintained at about 700° F. The length of run was 60 minutes. Pressure was 0.0 psig. The product yield and breakdown of hydrocarbon product is provided in Table 2 below.

TABLE 2

| PRODUCT YIELDS, WT. % OF CHARGE | |
|---|---|
| HYDROCARBONS | 39.36 |
| CO | 0.36 |
| H2O | 55.11 |
| METHANOL | 0.50 |
| DIMETHYL ETHER | 0.08 |
| COKE | 0.45 |
| H2 | 0.05 |
| WT. % RECOVERY | 95.92 |
| HYDROCARBON BREAKDOWN | |
| WT. % OF TOTAL HYDROCARBON | |
| METHANE | 1.20 |
| ETHANE | 0.23 |
| ETHENE | 4.44 |
| PROPANE | 7.92 |
| PROPENE | 4.42 |
| I-BUTANE | 20.54 |
| N-BUTANE | 2.06 |
| BUTENES | 3.37 |
| TOTAL C$_5$+ | 55.83 |
| AROMATICS | 30.06 |
| DURNE | 2.97 |

EXAMPLE 3

Methanol was passed in contact with ZSM-5 catalyst at a WHSV of 1.57 at a temperature maintained at about 700° F. Pressure was 0.0 psig. The product yield and hydrocarbon distribution are provided in Table 2 below.

TABLE 3

| PRODUCT YIELDS, WT. % OF CHARGE | |
|---|---|
| HYDROCARBONS | 40.54 |
| CO | 0.21 |
| H$_2$O | 53.57 |
| METHANOL | 3.18 |
| DIMETHYL ETHER | 1.22 |
| COKE | 0.05 |
| H$_2$ | 0.03 |
| WT. % RECOVERY | 98.80 |
| HYDROCARBON BREAKDOWN | WT. % OF TOTAL HYDROCARBON |
| METHANE | 0.93 |
| ETHANE | 0.20 |
| ETHENE | 8.45 |
| PROPANE | 3.05 |
| PROPENE | 8.42 |
| I-BUTANE | 13.53 |
| N-BUTANE | 1.26 |
| BUTENES | 6.34 |
| TOTAL C$_5$+ | 57.83 |
| AROMATICS | 22.47 |
| DURENE | 2.20 |

It will be observed from these data that significant yields of C$_5$+ hydrocarbons and isobutane were obtained. Also the percentage of durene was quite low.

Having thus generally described the invention and presented specific examples in support thereof, it is to be understood that no undue restrictions are to be imposed by reason thereof except as defined by the following claims.

We claim:

1. A method for converting a chemical reactant selected from the group consisting of methanol, ethanol, ether derivatives of lower alcohols and mixtures of alcohols and ethers to gasoline boiling range constituents with fluidizable catalyst particles comprising a crystalline zeolite having a pore dimension greater than about 5 Angstroms, a silica to alumina ratio of at least 12 and a constraint index within the range of 1 to 12 which comprises, maintaining said fluidizable catalysts particles flowing from the lower portion of a reaction zone to an upper portion thereof and through a plurality of adjacent and vertically spaced apart confined passageways in said reaction zone, said passageways arranged to promote a continuous upward flow of dispersed reactant, formed product thereof and suspended catalyst particles through the reaction zone, charging chemical reactant to the lower portion of said reaction zone as a plurality of separate streams each in alignment with a lower most confined passageway, recycling a plurality of separate confined catalyst streams from an upper portion of said reaction zone to a lower portion thereof so that recycled catalysts is discharged beneath and adjacent a lower most confined passageway, effecting temperature restraint in the reaction zone not to exceed about 1000° F. and imposing a temperature restraint in the chemical reactant and entrained catalyst in the lower portion of the reaction zone by effecting at least partial vaporization of the chemical reactant upon contact with hot recycled catalysts and thereafter passed upwardly through said confined passageways in said reaction zone.

2. The method of claim 1 wherein the upflowing methanol reactant and conversion products thereof are kept in contact with upflowing catalyst particles by dispersing the formation of significant gas bubbles.

3. The method of claim 1 wherein the catalyst comprises a ZSM-5 crystalline zeolite.

4. The method of claim 1 wherein the upflowing reactant and suspended particles of catalyst are caused to pass through a plurality of spaced apart gas bubble dispersal zones.

5. The method of claim 1 wherein the synthesis of durene is minimized by maintaining gasiform material in substantially upward plug flow arrangement during contact with the catalyst.

* * * * *